US00PP11784P2

(12) United States Plant Patent
Danziger

(10) Patent No.: US PP11,784 P2
(45) Date of Patent: Feb. 20, 2001

(54) TORENIA PLANT NAMED 'DANTOYHRT'

(75) Inventor: Gabriel Danziger, Nir Zvi (IL)

(73) Assignee: Danziger "Dan" Flower Farm, Post Beit Dagen (IL)

( * ) Notice: Under 35 U.S.C. 154(b), the term of this patent shall be extended for 0 days.

(21) Appl. No.: 09/129,221

(22) Filed: Aug. 5, 1998

(51) Int. Cl.[7] ..... A01H 5/00
(52) U.S. Cl. ..... Plt./263
(58) Field of Search ..... Plt./263

(56) References Cited

U.S. PATENT DOCUMENTS

P.P. 10,120 * 11/1997 Nagase ..... Plt./263

* cited by examiner

*Primary Examiner*—Bruce R. Campell
*Assistant Examiner*—Wendy A Baker

(57) ABSTRACT

The Torenia cultivar 'Dantoyhrt' is characterized by its four petals in violet-blue color of varying shades, with a prominent yellow spot on the lower petal; flower diameter of 35 mm; almost year-round flowering; cascading growth habit; dense branching; and ability to grow quickly.

1 Drawing Sheet

BACKGROUND OF THE INVENTION

The present invention comprises a new and distinct cultivar of Torenia, known by the cultivar name 'Dantoyhrt'. The cultivar 'Dantoyhrt' was selected as a naturally occurring, bud sport, color mutation of 'Torenia Pink Moon' at Moshav Mishmar Hashiva, Israel, by the inventor Gabriel Danziger in April 1997.

The first act of asexual reproduction of 'Dantoyhrt', was accomplished when vegetative cuttings were taken from the initial selection in May 1997 in a controlled environment in Mishmar Hashiva, Israel by a technician working under formulations established and supervised by the inventor. Horticultural examination of selected units initiated in July 1997 has demonstrated that the combination of characteristics as herein disclosed for 'Dantoyhrt' are firmly fixed and are retained through successive generations of asexual reproduction.

'Dantoyhrt' has not been observed under all possible environmental conditions. The phenotype may vary somewhat with variations in environment such as temperature, light intensity and day length, however, without any variations in genotype. The following observations, measurements and comparisons describe the plant grown in Mishmar Hashiva, Israel under greenhouse conditions which approximate those generally used in commercial practice.

BRIEF DESCRIPTION OF THE INVENTION

The following traits have been repeatedly observed and are determined to be basic characteristics of 'Dantoyhrt' which in combination distinguish this Torenia as a new and distinct cultivar:

1. Flower with four petals in violet-blue color of varying shades, with a prominent yellow spot on the lower petal;
2. Flower diameter of 35 mm;
3. Almost year-round flowering;
4. Cascading growth habit;
5. Evergreen, perennial, herbaceous plant;
6. Performs best in partial shade;
7. Recommended temperature range is 15–25° C.;
8. Requires constant fertilization and irrigation;

9. Densely branched plant, gracefully cascading from hanging baskets; and
10. Fast-growing plant.

Of the many commercial cultivars known to the present inventor, the most similar in comparison to 'Dantoyhrt' is 'Torenia Blue Moon'. The flowers of 'Dantoyhrt' are distinct from 'Torenia Blue Moon' because they have more intense violet-blue color and yellow spots on the lower petals.

BRIEF DESCRIPTION OF THE DRAWING

The accompanying photographic sheet shows typical flower and foliage characteristics of 'Dantoyhrt', with the color being as true as possible with illustrations of this type however, the colors recited in the specification should be considered to be controlling.

DETAILED BOTANICAL DESCRIPTION

In the following description color references are made to The Royal Horticultural Society (R.H.S.) Colour Chart. The color values were determined between 10:10 a.m. and 12:00 p.m. in April 1998 under full sunlight at Mishmar Hashiva, Israel.

Classification:
- *Botanical.*—A hybrid of Torenia sp.
- *Commercial.*—Torenia cultivar 'Dantoyhrt'.

Plant (general appearance):
- *Height.*—15 cm.
- *Growth habit.*—Cascading.
- *Spreading area.*—60 cm.
- *Blooming period.*—Plants begin flowering soon after rooting and continue almost all year round except for winter.
- *Cold tolerance.*—At temperatures between 0°–10° C., the plant stops growing, becomes deformed and turns purple; at temperatures below 0° C., the plant dies.
- *Vigor.*—Well-grown, densely-branched plant measuring 50 cm in width and 60 cm in length is achieved in 8–10 weeks, depending on growing conditions.

Stem:

*Color.*—Yellow-Green R.H.S. 146B.

*Thickness.*—3 mm.

*Pubescence.*—Medium.

*Branching.*—Strong.

*Length of internode.*—6 cm.

Leaf:

*Arrangement on stem.*—Opposite.

*Shape.*—Overall: Oval. Base: Heart-shaped. Tip: Acuminate. Margin: Serrate.

*Size.*—Length is 4 cm and width is 3.5 cm.

*Thickness.*—1 mm.

*Color of upper surface.*—Yellow-Green R.H.S. 146A to 147A, depending on fertilization rates and growing conditions.

*Color of lower surface.*—Yellow-green, R.H.S. 146B, or slightly brighter.

*Markings.*—None.

*Pubescence.*—Weak.

Flower:

*Orientation at opening.*—Upward.

*Type.*—Single.

*Shape.*—Funnelform.

*Diameter.*—35 mm.

*Depth.*—Approximately 2.5 cm.

*Color.*—The top petal is uniformly R.H.S. 91A in coloration, with only the margins darkening to R.H.S. 92A with age. The two side petals are R.H.S. 89B in coloration, and the lower petal coloration consists of 4 color zones: an inner zone (spot) of R.H.S. 2A, encircled by a zone of R.H.S. 93B, followed by a zone of R.H.S. 91A and finishing towards the margin with another zone of R.H.S. 93B.

*Bud.*—Shape: Ellipsoidal, five-lobed. Size: Approximately 18 mm in length and 9 mm in diameter. Color: Green, R.H.S. 143A.

*Peduncle* (*length and color*).—25 mm, Yellow-Green R.H.S. 144A.

*Petals.*—The superior and lateral petals open less than perpendicular to the pedicel and the inferior petal is reflexed so that the plane of the flower surface is not flat. Number of petals: Four (4) petals, all overlapping. Shape: Ellipsoidal with the lower petal having a broad base. Color of throat: The ground color of the lower portion of the flower throat is R.H.S. 10B, blending into a coloration of R.H.S. 2A in the upper portion of the flower throat. The venation of the flower throat is R.H.S. 90B.

Reproductive organs:

*Pistil* (*number and color*).—One (1), violet R.H.S. 84B.

*Stamens* (*number*).—Four (4).

*Anther* (*color*).—White R.H.S. 155A.

*Filament* (*color*).—White R.H.S. 155C.

*Seed/Fruit.*—The plant is not fertile; no seeds have been observed.

Resistance: Under normal growing conditions which include regular spraying, no susceptibility to pests was observed. However, powdery mildew does occur and can be controlled by spraying.

I claim:

1. A new and distinct Torenia plant named 'Dantoyhrt' substantially as illustrated and described.

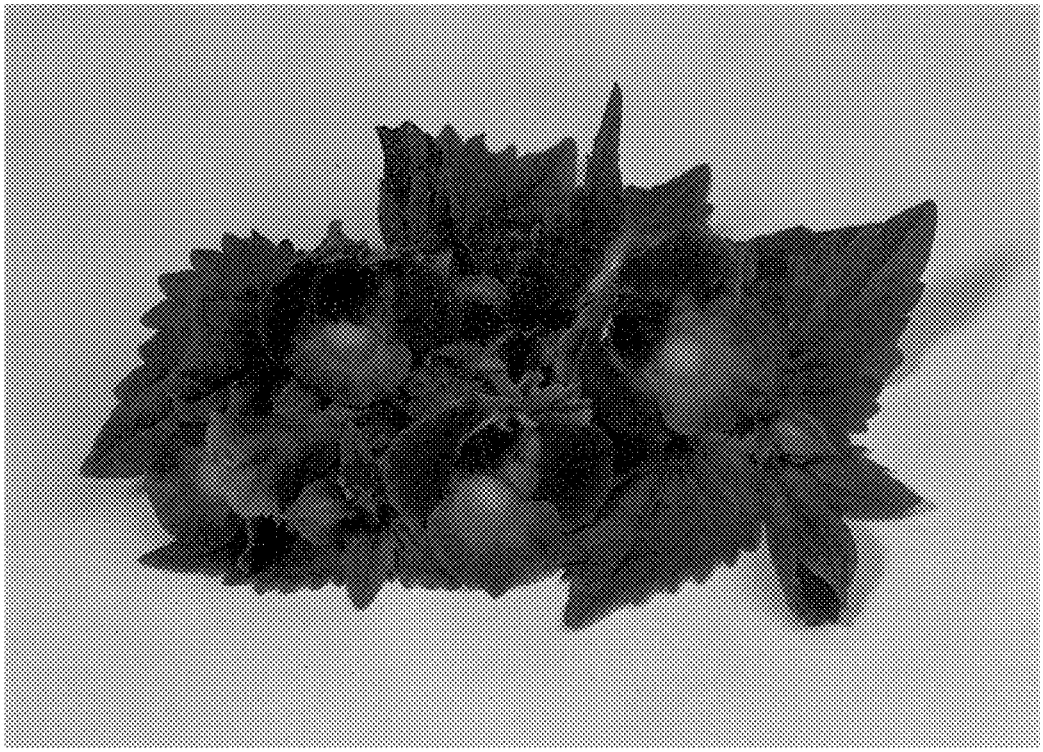

* * * * *